(12) United States Patent
Shen et al.

(10) Patent No.: US 9,209,824 B2
(45) Date of Patent: Dec. 8, 2015

(54) ULTRA LOW POWER INTERFACE USING ADAPTIVE SUCCESSIVE APPROXIMATION REGISTER

(71) Applicant: Medtronic, Inc., Minneapolis, MN (US)

(72) Inventors: Xiaonan Shen, Shoreview, MN (US); Jonathan P. Roberts, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/182,318

(22) Filed: Feb. 18, 2014

(65) Prior Publication Data

US 2015/0073228 A1    Mar. 12, 2015

Related U.S. Application Data

(60) Provisional application No. 61/876,447, filed on Sep. 11, 2013.

(51) Int. Cl.
*H03M 1/12* (2006.01)
*H03M 1/38* (2006.01)
*A61B 5/04* (2006.01)
*H03M 1/00* (2006.01)
*A61B 5/00* (2006.01)
(Continued)

(52) U.S. Cl.
CPC ............ *H03M 1/007* (2013.01); *A61B 5/0031* (2013.01); *A61B 5/042* (2013.01); *A61B 5/0428* (2013.01); *H03M 1/12* (2013.01); *H03M 1/462* (2013.01); *A61B 5/0215* (2013.01); *A61B 5/0476* (2013.01); *A61B 5/0488* (2013.01); *A61B 5/0538* (2013.01); *A61B 5/1118* (2013.01); *A61B 2560/0209* (2013.01)

(58) Field of Classification Search
CPC ............... H03M 1/002; H03M 1/007; H03M 1/38–1/462
See application file for complete search history.

(56) References Cited

U.S. PATENT DOCUMENTS 4,839,649 A     6/1989  Imai
5,543,795 A *   8/1996  Fernald ...................... 341/163
(Continued)

FOREIGN PATENT DOCUMENTS

JP          11154866 A  *  6/1999
JP        2006108893 A  *  4/2006
WO    WO 2012/126003 A1     9/2012

OTHER PUBLICATIONS

Stankovic et al., Power Reduction Technique for Successive-Approximation Analog-to-Digital Converters, 8th International Conference on Telecommunications in Modern Satellite, Cable and Broadcasting Services, 2007. TELSIKS 2007, IEEE Sep. 2007.*

(Continued)

*Primary Examiner* — Howard Williams
(74) *Attorney, Agent, or Firm* — Evans M. Mburu

(57) ABSTRACT

A medical device and associated method convert an analog signal using an adaptable bit number. The medical device includes an analog-to-digital (A/D) converter for receiving an analog signal. The A/D converter has a full scale range and a total number of bits spanning the full scale range. The A/D converter converts the analog signal to a digital signal over conversion cycles using an adaptable bit number so that on at least a portion of the conversion cycles an adapted number of bits spanning a portion of the full scale range less than the total number of bits is used by the A/D converter to convert the analog signal.

20 Claims, 8 Drawing Sheets

(51) Int. Cl.
   *H03M 1/46* (2006.01)
   *A61B 5/042* (2006.01)
   *A61B 5/0428* (2006.01)
   *A61B 5/0215* (2006.01)
   *A61B 5/0476* (2006.01)
   *A61B 5/0488* (2006.01)
   *A61B 5/11* (2006.01)
   *A61B 5/053* (2006.01)

(56) References Cited

U.S. PATENT DOCUMENTS

| | | | |
|---|---|---|---|
| 5,593,431 A | 1/1997 | Sheldon | |
| 6,044,297 A | 3/2000 | Sheldon | |
| 6,504,863 B1 | 1/2003 | Hellmark | |
| 6,811,538 B2 | 11/2004 | Levendowski | |
| 2002/0077568 A1 | 6/2002 | Haddock | |
| 2005/0273170 A1 | 12/2005 | Navarro | |
| 2007/0208262 A1 | 9/2007 | Kovacs | |
| 2009/0167587 A1 | 7/2009 | Xu | |
| 2011/0022127 A1 | 1/2011 | Averina | |
| 2013/0135125 A1 | 5/2013 | Schreiner et al. | |

OTHER PUBLICATIONS (PCT/US2014/054196) PCT Notification of Transmittal of the International Search Report and the Written Opinion of the International Searching Authority.

\* cited by examiner

ULTRA LOW POWER INTERFACE USING ADAPTIVE SUCCESSIVE APPROXIMATION REGISTER

TECHNICAL FIELD

The disclosure relates to medical devices capable of converting analog signals to digital signals using an adaptive number of bits.

BACKGROUND

Numerous implantable medical devices (IMDs) are available for acute or chronic implantation within patients. Some implantable medical devices may be used to monitor physiological signals of the patient, such as cardiac pacemakers, implantable hemodynamic monitors, implantable cardiac monitors (sometimes referred to as implantable loop recorders or ECG monitors), implantable blood chemistry monitors, implantable pressure monitors, etc. Among the various types of physiological sensors utilized by medical devices for monitoring patients are electrodes for measuring electrical signals and/or impedances, piezoelectric crystals, accelerometers, pressure sensors, pH sensors, acoustical sensors, temperature sensors, and oxygen sensors.

The physiological signals may be stored, processed and analyzed by the medical device to generate physiological data about a patient useful to a clinician in diagnosing a condition or planning medical treatment. Some implantable devices may be configured to deliver a therapy in conjunction with monitoring of physiological signals. Physiological signals may be processed and analyzed to determine when a therapy is needed or how a therapy needs to be adjusted to benefit the patient. Therapies delivered by an implantable medical device can include electrical stimulation therapies, e.g., cardiac pacing, cardioversion/defibrillation shock pulses, or neurostimulation, and pharmacological or biological fluid delivery therapies.

In order to provide the physiological data needed for detecting pathological conditions, controlling automatic therapy delivery or generating data in a form useful to a clinician for diagnosis and prognosis, an analog signal produced by a physiological sensor often needs to be digitized. An analog-to-digital (A/D) converter is used to convert the analog signal to a digital signal according to a desired sampling rate and bit resolution. When physiological signals are monitored continuously or on a frequent basis, A/D converters included in an IMD can contribute significantly to the overall device power consumption.

An ongoing design goal in medical device technology is device size reduction, e.g. to enable minimally invasive implant procedures and to promote patient comfort. Reduction of device size, however, poses limitations on the space available for power supplies, signal processing circuitry, and other device components that support the primary device function. Systems and methods that reduce the power consumption required by signal processing circuitry, such as A/D converters, can improve the battery longevity of implantable devices and/or contribute to an overall size reduction.

SUMMARY

In general, the disclosure is directed towards techniques for converting analog signals to digital signals in medical devices. A self-adjusting A/D converter including an adaptable successive approximation register (ASAR) and conversion control module converts an analog input signal to a digital signal using an adaptable number of bits. In one embodiment, a method for converting an analog signal to a digital signal includes receiving an analog signal by an A/D converter. The A/D converter has a full scale range and a total number of bits spanning the full scale range. The method further includes converting the analog signal to a digital signal over conversion cycles using an adaptable bit number so that on at least a portion of the conversion cycles an adapted number of bits less than the total number of bits spanning the full scale range is used by the A/D converter to convert the analog signal. The adapted number of bits spans a portion of the full scale range that is less than the full scale range.

In another embodiment, a medical device includes an analog-to-digital (A/D) converter configured to receive an analog signal. The A/D converter has a full scale range and a total number of bits spanning the full scale range. The A/D converter includes an ASAR configured to convert the analog signal to a digital signal over conversion cycles using an adaptable bit number. On at least a portion of the conversion cycles, an adapted number of bits that spans a portion of the full scale range less than the total number of bits is used to convert the analog signal.

In another example, a medical device includes receiving means for receiving an analog signal, converting means for converting the analog signal to a digital signal over conversion cycles, and controlling means for adjusting an adaptable number of bits used by the converting means for converting the analog signal over the conversion cycles. The adaptable number of bits spans less than a full scale range of the converting means for at least one of the conversion cycles.

In other examples, a computer readable storage medium stores a set of instructions executable by a control module of an analog-to-digital (A/D) converter included in a medical device. The instructions cause the control module to enable the A/D converter to convert an analog signal to a digital signal over conversion cycles using an adaptable bit number. The instructions further cause the control module to adjust the adaptable bit number so that on at least a portion of the conversion cycles an adapted number of bits is used to convert the analog signal. The adapted number of bits spans a portion of a full scale range of the A/D converter less than the full scale range spanned by the total number of available bits of the A/D converter.

The details of one or more aspects of the disclosure are set forth in the accompanying drawings and the description below. Other features, objects, and advantages will be apparent from the description and drawings, and from the claims.

DETAILED DESCRIPTION

Figure 1:
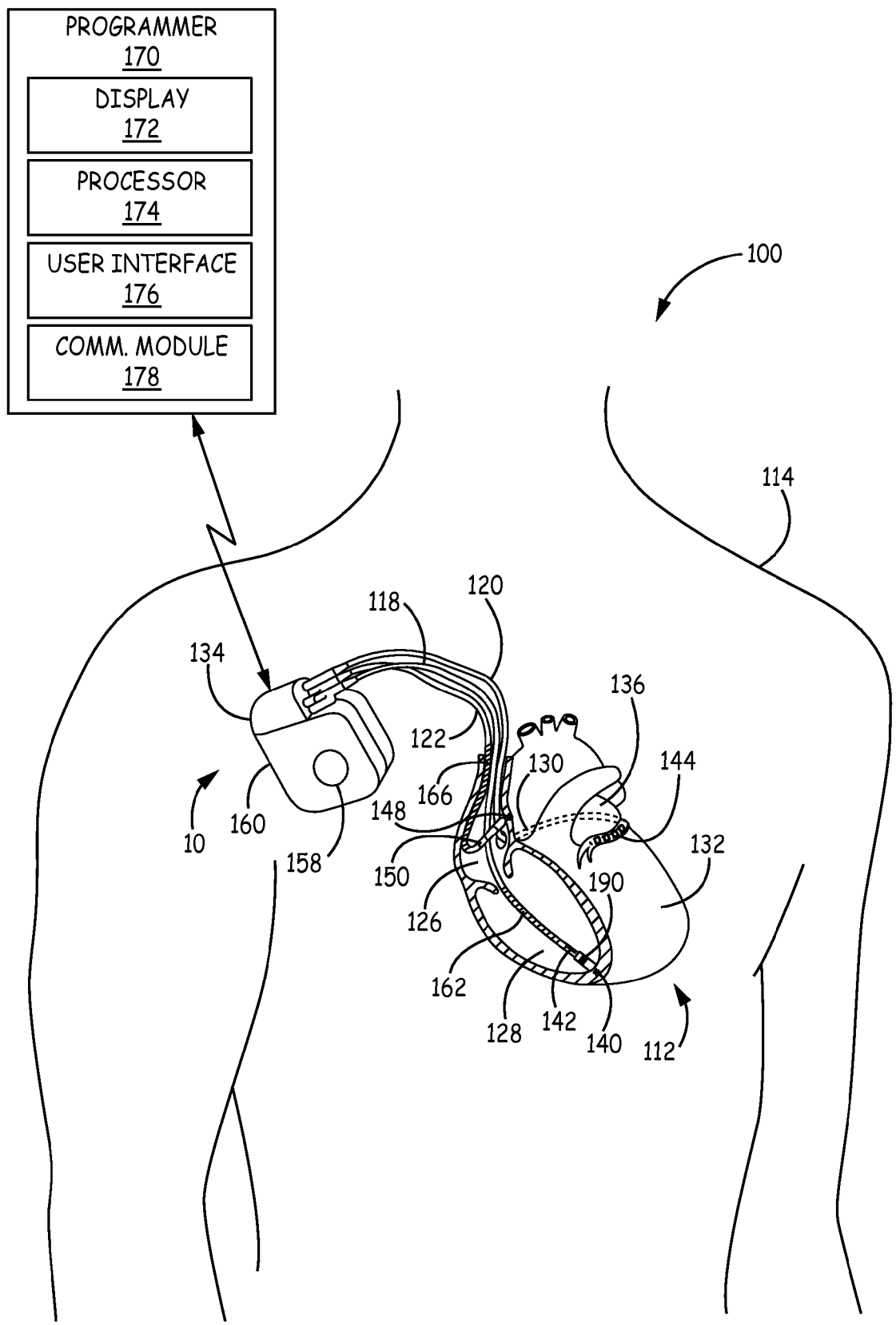
FIG. 1 is a schematic diagram of one embodiment of an implantable medical device (IMD) system.

FIG. 1 is a schematic diagram of one embodiment of an implantable medical device (IMD) system 100. System 100 includes one or more sensors of physiological signals, which may include electrical signals, mechanical signals, chemical signals, or temperature signals, received by processing circuitry within IMD 10. IMD signal processing circuitry includes an A/D converter for converting an analog signal to a digital signal. The A/D converter includes an adaptive successive approximation register (ASAR) for reducing the power required by the signal processing circuitry for converting a sensed analog signal to a digital signal as will be described herein. Accordingly, the disclosed apparatus and techniques may be implemented in a wide variety of medical devices, including implantable and external devices.

Examples of implantable medical devices in which the signal processing techniques disclosed herein may be implemented include cardiac pacemakers, implantable cardioverter defibrillators (ICDs), cardiac monitors such as hemodynamic monitors or ECG recorders, neurostimulators configured for delivering electrical stimulation to and monitoring activity of peripheral nerves and/or portions of the central nervous system, electroencephalogram (EEG) monitors, electromyogram (EMG) monitors, drug pumps or other fluid delivery devices, oxygen monitors, flow monitors, pressure monitors, impedance monitors, acoustical monitors, activity monitors, motion monitors, or any other implantable device configured for sensing a physiological signal. The apparatus and techniques disclosed herein may alternatively be implemented in an external device which may be a wearable patient monitor or a bedside patient monitor. The system 100 shown in FIG. 1 is one illustrative example of an implantable medical device system that includes an IMD 10 configured to sense physiological signals and utilize A/D conversion to enable signal analysis and detection of a physiological event or condition and/or a need for therapy.

System 100 includes IMD 10 coupled to leads 118, 120, and 122 which carry multiple electrodes. IMD 10 is configured for bidirectional communication with programmer 170. IMD 10 may be, for example, an implantable pacemaker or implantable cardioverter defibrillator (ICD) that provides electrical signals to heart 112 via electrodes coupled to one or more of leads 118, 120, and 122 for pacing, cardioverting and defibrillating the heart 112. IMD 10 is capable of delivering pacing in one or more heart chambers, and in the embodiment shown, is configured for multi-chamber pacing and sensing in the right atrium (RA) 126, the right ventricle (RV) 128, and the left ventricle (LV) 132 using leads 118, 120 and 122.

IMD 10 delivers RV pacing pulses and senses RV intracardiac electrogram (EGM) signals using RV tip electrode 140 and RV ring electrode 142. RV lead 118 is shown to carry a coil electrode 162 which may be used for delivering high voltage cardioversion or defibrillation shock pulses. IMD 10 senses LV EGM signals and delivers LV pacing pulses using the electrodes 144 carried by a multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and delivering LA pacing pulses. RV lead 118 is further shown to carry a sensor 190, which may be a pressure sensor, accelerometer, oxygen sensor, or other type of physiological sensor generating an analog signal that may be converted to a digital signal for analysis by IMD 10.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 may detect tachyarrhythmias of heart 112, such as fibrillation of ventricles 128 and 132, and deliver high voltage cardioversion or defibrillation therapy to heart 112 in the form of electrical shock pulses. Pacing and sensing of the cardiac chambers is typically achieved using the pace/sense electrodes 140, 142, 144, 148 and 150, however in some embodiments coil electrodes 162 and/or 166 may be used in sensing and/or pacing electrode vectors.

While IMD 10 is shown in a right pectoral implant position in FIG. 1, a more typical implant position, particularly when IMD 10 is embodied as an ICD, is a left pectoral implant position. In other embodiments, IMD 10 may be implanted in an abdominal location.

IMD 10 includes internal circuitry for performing the functions attributed to IMD 10. Housing 160 encloses the internal circuitry. It is recognized that the housing 160 or portions thereof may be configured as an active electrode 158 for use in cardioversion/defibrillation shock delivery or used as an indifferent electrode for unipolar pacing or sensing configurations with any electrodes carried by leads 118, 120 and 122. IMD 10 includes a connector block 134 having connector bores for receiving proximal lead connectors of leads 118, 120 and 122. Electrical connection of electrodes or other sensors carried by leads 118, 120 and 122 and IMD internal circuitry is achieved via various connectors and electrical feedthroughs included in connector block 134.

While a multi-chamber ICD is shown in FIG. 1, it is recognized that techniques disclosed herein may be implemented in numerous types of implantable medical devices, including single, dual chamber and multi-chamber pacemakers, with or without anti-arrhythmia therapies such as cardioversion and defibrillation shock capabilities and any other examples of medical devices listed herein.

Programmer 170 includes a display 172, a processor 174, a user interface 176, and a communication module 178 including wireless telemetry circuitry for communication with IMD 10. In some examples, programmer 170 may be a handheld device or a microprocessor-based home monitor or bedside programming device. A user, such as a physician, technician, nurse or other clinician, may interact with programmer 170 to communicate with IMD 10. For example, the user may interact with programmer 170 via user interface 176 to retrieve currently programmed operating parameters, physiological data collected by IMD 10, or device-related diagnostic information from IMD 10. A user may also interact with programmer 170 to program IMD 10, e.g., select values for operating parameters of the IMD.

Programmer 170 includes a communication module 178 to enable wireless communication with IMD 10. Examples of communication techniques used by system 100 include low frequency or radiofrequency (RF) telemetry, which may be an RF link established via Bluetooth, WiFi, or MICS for example. In some examples, programmer 170 may include a programming head that is placed proximate to the patient's body near the IMD 10 implant site, and in other examples programmer 170 and IMD 10 may be configured to communicate using a distance telemetry algorithm and circuitry that does not require the use of a programming head and does not require user intervention to maintain a communication link.

The A/D conversion techniques disclosed herein may be implemented in programmer 170 for processing signals received from IMD 10 and/or for processing signals acquired directly by programmer 170, e.g. ECG signals using external surface electrodes.

It is contemplated that programmer 170 may be coupled to a communications network via communications module 178 for transferring data to a remote database or computer to allow remote monitoring and management of patient 114 using the techniques described herein.

Figure 2:
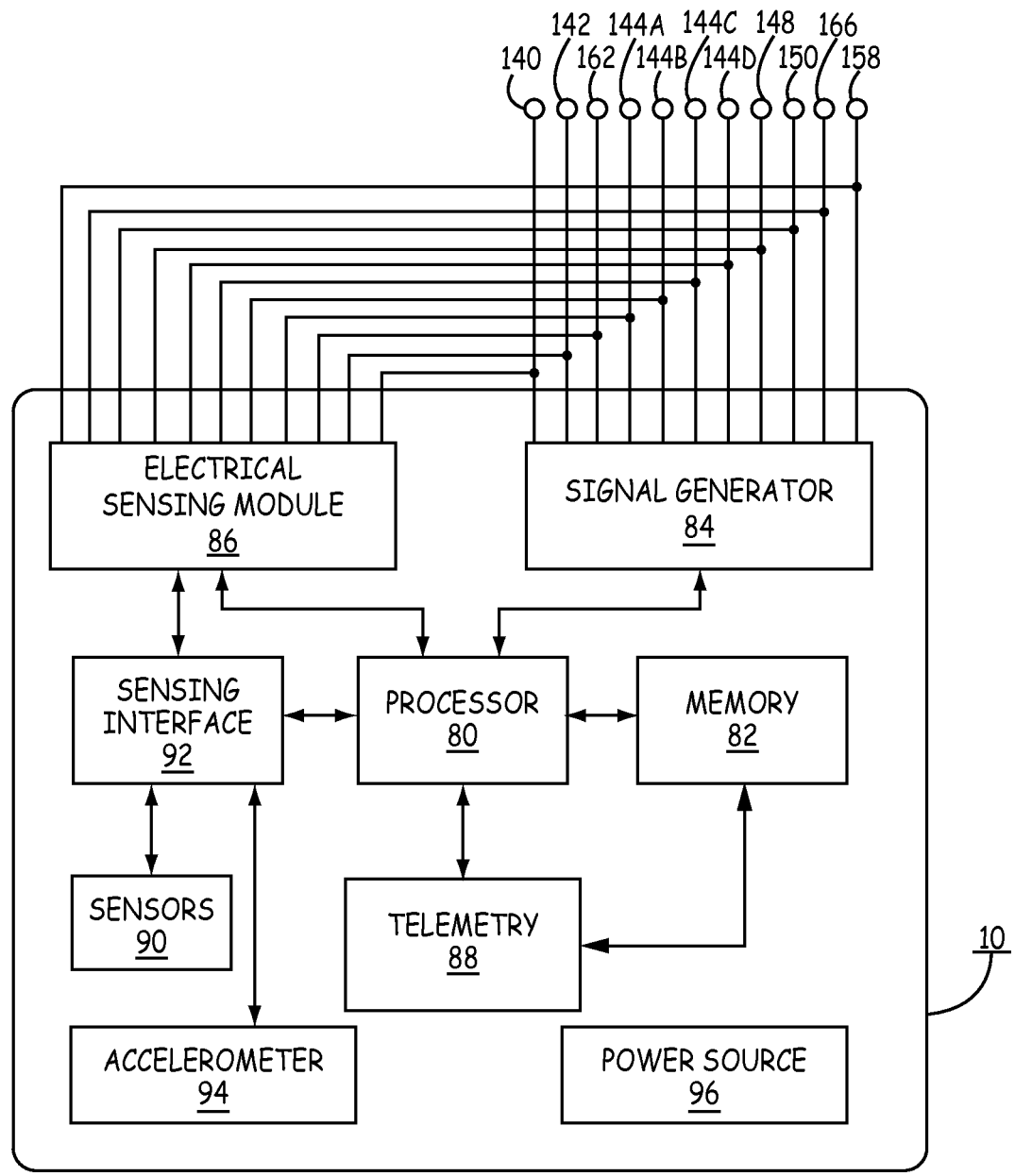
FIG. 2 is a functional block diagram of an example configuration of the IMD shown in FIG. 1

FIG. 2 is a functional block diagram of an example configuration of IMD 10. In the example illustrated by FIG. 2, IMD 10 includes a processor and control module 80, also referred to herein as "processor" 80, memory 82, signal generator 84, electrical sensing module 86, and telemetry module 88. IMD 10 may additionally include an accelerometer 94 for detecting motion or position, such as patient activity or posture, cardiac motion, respiratory motion or other physiological movement. IMD 10 optionally includes other physiological sensors 90, which may include pressure sensors, pH sensors, temperature sensors, acoustical sensors, flow sensors, oxygen sensors, piezoelectric sensors or any other sensor used for producing a signal responsive to a time-varying physiological condition. Accelerometer 94 and sensors 90 are shown schematically within IMD 10, however it is recognized that accelerometer 94 and sensors 90 may alternatively be carried by a lead 118, 120 or 122 extending from IMD 10, such as sensor 190 shown in FIG. 1, mounted along IMD housing 160, or positioned within or along connector block 134.

Modules 80, 84, 86, 88, 92, memory 82, sensors 90, and accelerometer 94 shown in FIG. 2 may include any discrete and/or integrated electronic circuit components that implement analog and/or digital circuits capable of producing the functions attributed to IMD 10 herein. For example, sensing module 86, sensing interface 92, and processor and control module 80 may include analog circuits, e.g., amplification circuits, filtering circuits, and/or other analog circuitry for receiving and processing signals from electrodes 140, 142, 162, 144, 148, 150, 158, 162 and 166, sensors 90 and accelerometer 94. Sensing module 86, sensing interface 92 and processing and control module 80 may also include digital circuits, e.g., combinational or sequential logic circuits, memory devices, A/D converters, etc. for processing received signals.

The functions attributed to IMD 10 herein may be embodied as one or more processors, hardware, firmware, software, or any combination thereof. Depiction of different features as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components. For example, sensing interface 92 for receiving and converting analog electrical signals received from other IMD modules or sensors may be implemented in hardware and software included in processor 80 and memory 82.

In some examples, sensing interface 92 is configured to receive one or more analog signals from electrical sensing module 86, sensors 90, and/or accelerometer 94. Sensing interface 92 includes an A/D converter for converting analog signals to digital signals. Processor 80 receives the converted digital signals and may analyze the digital signals for detecting a patient condition, controlling a therapy delivered by signal generator 84, and/or storing patient data in memory 82 for later transmission via telemetry module 88. As will be described in greater detail herein, the A/D converter included in sensing interface 92 uses an ASAR having an adjustable number of bits used to convert an analog signal to a digital signal.

A power source 96 provides power to each of the other modules and components of IMD 10 as required. Processor 80 may execute power control operations to control when various components or modules are powered to perform various IMD functions. Power source 96 may include one or more energy storage devices, such as one or more rechargeable or non-rechargeable batteries. Processor 80 may also be configured to perform diagnostic testing of IMD 10, which may include monitoring the remaining charge of power source 96 and providing a replacement or recharge indicator, for example. The connections between power source 96 and processor 80 and other IMD modules and components are not shown for the sake of clarity.

In some examples, sensing interface 92 may receive internal IMD signals from power source 96, signal generator 84, processor 80 or other IMD modules or components for digitizing signals for use in device diagnostic testing, such as testing charging or output circuitry included in signal generator 84, testing charge of power source 96, validating or coding/decoding communication signals received or produced by telemetry 88, or other device functions. Accordingly, sensing interface 92 may be configured to convert one or more analog signals, which may be physiological signals received from sensors 90, accelerometer 94, or electrical sensing module 86 and/or device-related signals produced by internal IMD circuits or modules such as power source 96, telemetry module 88 or signal generator 84.

Memory 82 may include computer-readable instructions that, when executed by processor 80, cause IMD 10 and processor 80 to perform various functions attributed throughout this disclosure to IMD 10, processor 80, and sensing interface 92. The computer-readable instructions may be encoded within memory 82. Memory 82 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

Processor and control module 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, sensing interface 92 may, at least in part, be stored or encoded as instructions in memory 82 that are executed by processor and control module 80.

Processor and control module 80 includes a therapy control module that controls signal generator 84 to deliver electrical stimulation therapy, e.g., cardiac pacing, to heart 112 according to a selected one or more therapy programs, which may be stored in memory 82. Signal generator 84 is electrically coupled to electrodes 140, 142, 144A-144D (collectively 144), 148, 150, 158, 162, and 166 (all of which are shown in FIG. 1), e.g., via conductors of the respective leads 118, 120, 122, or, in the case of housing electrode 158, via an electrical conductor disposed within housing 160 of IMD 10. Signal generator 84 is configured to generate and deliver electrical stimulation therapy to heart 112 via selected combinations of electrodes 140, 142, 144, 148, 150, 158, 162, and 166. Signal generator 84 delivers cardiac pacing pulses according to therapy control parameters and responsive to signals sensed by electrical sensing module, sensors 90, and accelerometer 94. Memory 82 stores intervals, counters, or other data used by processor 80 to control the delivery of pacing pulses by signal generator 84.

Signal generator 84 may include a switch module (not shown) and processor and control module 80 may use the switch module to select, e.g., via a data/address bus, which of the available electrodes are used to deliver pacing pulses. Processor 80 controls which of electrodes 140, 142, 144A-144D, 148, 150, 158, 162, and 166 is coupled to signal generator 84 for delivering stimulus pulses, e.g., via the switch module. The switch module may include a switch array, switch matrix, multiplexer, or any other type of switching device suitable to selectively couple a signal to selected electrodes.

Electrical sensing module 86 monitors cardiac electrical signals for sensing cardiac electrical events, e.g. P-waves and R-waves, from selected ones of electrodes 140, 142, 144A-144D, 148, 150, 158, 162, or 166 in order to monitor electrical activity of heart 112. Sensing module 86 may also include a switch module to select which of the available electrodes are used to sense the cardiac electrical activity. In some examples, processor 80 selects the electrodes to function as sense electrodes, or the sensing vector, via the switch module within sensing module 86.

Sensing module 86 may include multiple sensing channels, each of which may be selectively coupled to respective combinations of electrodes 140, 142, 144A-144D, 148, 150, 158, 162, or 166 to detect electrical activity of a particular chamber of heart 112. Each sensing channel may comprise an amplifier that outputs an indication to processor 80 in response to sensing of a cardiac depolarization, in the respective chamber of heart 112. In this manner, processor 80 may receive sense event signals corresponding to the occurrence of R-waves and P-waves in the various chambers of heart 112, e.g. ventricular sense events and atrial sense events corresponding to intrinsic depolarization of the respective heart chamber.

Sensing module 86 may further provide analog signals received via electrodes 140, 142, 144A-144D, 148, 150, 158, 162, and 166 to sensing interface 92 for conversion to digital signals. For example, digitized EMG signals may be analyzed by processor 80 for detecting and discriminating cardiac arrhythmias, detecting T-wave alternans, detecting cardiac ischemia or other cardiac conditions. Accordingly, sensing interface 92 may include multiple A/D converters corresponding to each of the sensing channels included in sensing module 86. Other electrical signals that may be received from electrical sensing module 86 may include electrical impedance signals that may be used to monitor lead impedance, cardiac impedance, thoracic impedance or other impedance values of interest.

Accelerometer 94 may be embodied as a one-dimensional, two-dimensional, or three-dimensional accelerometer including one or more DC or AC accelerometers or other motion sensitive devices. Examples of accelerometers used for sensing patient activity and/or posture are generally described in U.S. Pat. No. 5,593,431 (Sheldon), and U.S. Pat. No. 6,044,297 (Sheldon), both of which are hereby incorporated herein by reference in their entirety. An accelerometer signal used for monitoring patient activity may be analyzed for providing an activity-indicated heart rate for controlling cardiac pacing or for other patient monitoring, therapy control or diagnostic purposes.

In one example, an A/D converter included in sensing interface 92 for receiving an accelerometer signal may have a full scale range of ±2 G to encompass earth gravity (1G) plus a 1G range that covers typical human activities. The full scale range of 4G, (−2G to +2G) accommodates instances when the orientation of the accelerometer changes resulting in a signal polarity change. A majority of time a patient will be at relatively low levels of activity, e.g. resting or normal activities of daily living, such that the accelerometer signal will vary within only a portion of the full scale range of the A/D converter. Less often, the accelerometer signal amplitude may extend close to the full range of the A/D converter for brief periods time, e.g. during bouts of high levels of physical activity or exertion. Generally, the accelerometer signal will vary within a smaller range than the full scale range of the A/D converter during any given activity level. The variation will remain within a smaller range than the full scale range for a vast majority of the time for most patients.

Digital conversions utilizing the full scale range of the A/D converter for every sample point of an accelerometer signal are, therefore, consuming power to convert bits that may not need to be utilized on every conversion cycle. An ASAR as disclosed herein utilizes an adaptable number of bits on each conversion cycle to conserve power consumption by the A/D converter. An A/D converter having an ASAR and associated conversion techniques as disclosed herein are appropriate for use with an analog signal that requires a relatively large full scale range but typically remains within only a portion of that range for extended periods of time.

As described herein, the sensing interface 92 may include one or more A/D converters each having an ASAR for converting a received signal using an adaptable bit number. The adaptable bit number may be reduced from the full scale bit number to reduce the time required to convert an analog signal sample to a digital signal. An A/D conversion cycle is the time required to convert an analog signal sample point to an N-bit digital word. A/D conversion is normally performed bit-by-bit to set each bit to a digital high or digital low value for all N bits. A conversion cycle is not completed until all available bits in the N-bit digital word have been set. The duration of a conversion cycle can be referred to as the "bit time" and is normally equal to the total number of available bits used to cover the full scale range of an A/D converter. For example, if an 8-bit A/D converter is used, a single conversion cycle with require a bit time of 8. An ASAR as disclosed herein enables an overall reduction in the average conversion cycle bit time by using an adaptable number of bits which is less than the total number of available bits for at least some conversion cycles. A reduction in overall average bit time conserves the IMD power supply.

A patient activity or posture signal that does not vary rapidly relative to a sampling rate and that remains within a smaller range than the full scale A/D converter range for extended periods of time is one illustrative example of a signal that may be converted using the methods described herein to significantly reduce the overall average bit time. Numerous other physiological and/or internal IMD signals may be converted using the methods disclosed herein to conserve power by reducing the average conversion cycle time. Sensing interface 92 may therefore receive signals from any of accelerometer 94, sensors 90, electrical sensing module 86, or any internal IMD components or modules and may include a required number of A/D converters having ASARs for converting the received analog signals.

Figure 3:
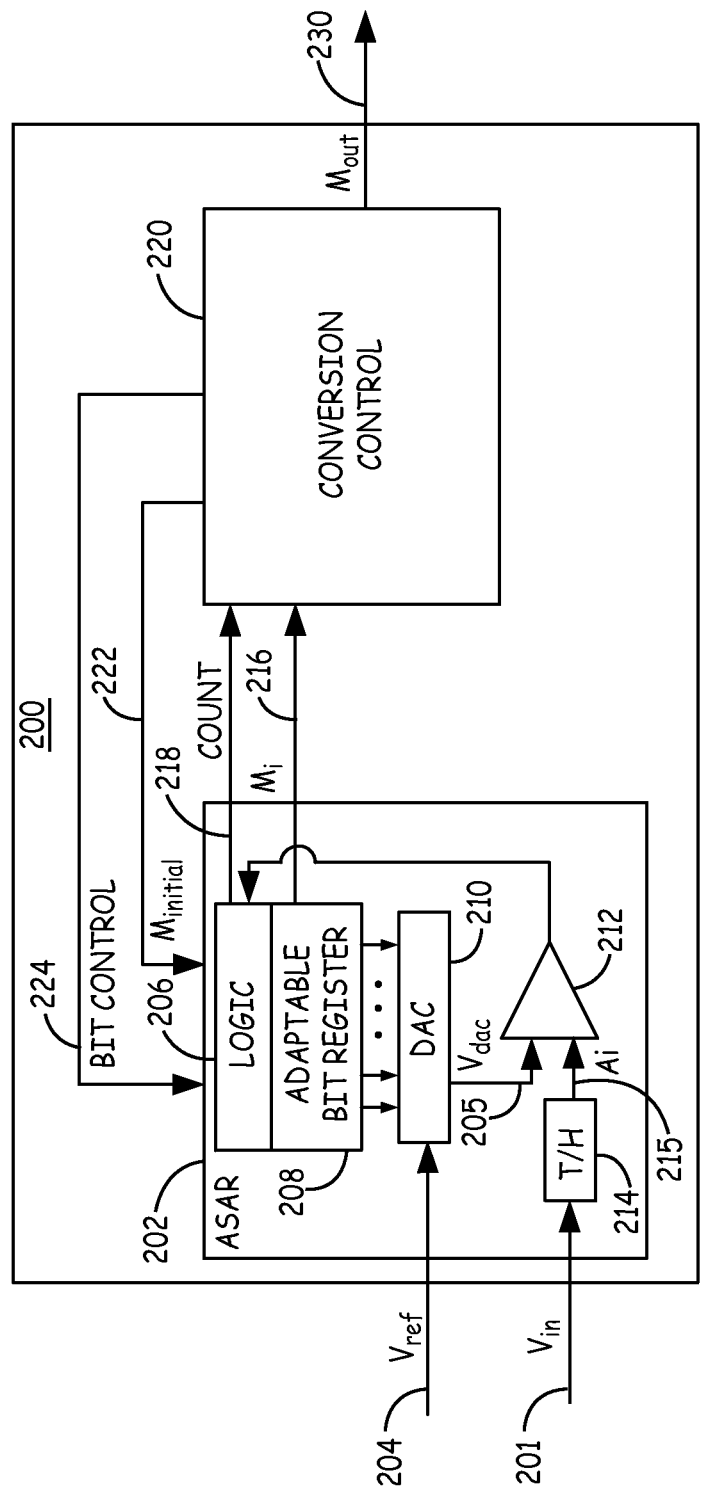
FIG. 3 is schematic diagram of an A/D converter that may be included in a sensing interface of the IMD shown in FIG. 2.

FIG. 3 is schematic diagram of an A/D converter 200 that may be included in sensing interface 92 of IMD 10. A/D converter includes an ASAR 202 and a conversion control module 220. A/D converter 200 is a self-adjusting A/D converter that uses an automatically adjusted number of bits for converting an analog input signal Vin 201 to a digitized output signal Mout 230. Vin 201 may be received from any physiological sensor such as those described or listed herein. In one example, Vin 201 is a signal produced by accelerometer 94 for monitoring patient activity and/or posture. In other examples, Vin 201 is an ECG signal, EMG signal, EEG signal, pressure signal, oxygen signal, pH signal, temperature signal, acoustical signal, or an impedance signal. Alternatively Vin 201 may be an internal device-generated signal received from other IMD circuitry and used for device diagnostic testing.

Vin 201 is received by ASAR 202. ASAR 202 includes a track and hold circuit 214 to sample the analog input signal Vin 201 at a desired sampling rate and hold the value of an analog signal sample Ai 215 during a conversion cycle. The illustrative embodiments described herein pertain to a voltage converter. The conversion techniques disclosed herein however, may be utilize an adaptive number of bits for any conversion that uses successive approximations to generate a digitized sequence of results. For example, the techniques disclosed herein may be utilized in converters configured to convert current, resistance, capacitance, light intensity, or other received signals.

During the conversion cycle, ASAR 202 performs a search algorithm to converge upon a digital estimation of Ai 215. In one example, ASAR 202 performs a bit-by-bit binary search to determine a digital word representation of the analog signal sample Ai 215. The binary search includes comparing Ai 215 to an approximated voltage signal Vdac 205. Vdac 205 is an analog voltage signal produced by digital-to-analog (DAC) converter 210 included in ASAR 202. DAC 210 receives a digital "guess" or approximation of Mi, the digitized value of Ai 215, from adaptable bit register 208. The digital approximation of Mi is converted to an analog signal Vdac 205 for comparing to Ai 215 by comparator 212 during the binary search algorithm. DAC 210 converts the digital approximation of Mi to Vdac 205 using an input signal Vref 204. Vref 204 may be an input voltage signal provided by power supply 96. Vref 204 may be equal to the full range of A/D converter 200 when A/D converter 200 has a range from 0V to +Vref or may be equal to half the full scale range when A/D converter 200 has a range from −Vref to +Vref.

In past A/D converters that utilize a successive approximation register (SAR), the SAR converts an analog input signal to a digital word using successive approximations of an analog signal sample in a search algorithm. Typically, an A/D converter using a SAR will perform a binary search by initially approximating the analog signal sample to be equal to the midway point of the full-scale range of the A/D converter, e.g. Vref/2 for a range from 0 to Vref or a midway point of 0 V when the full scale range is −Vref to +Vref. This midway point would correspond to a most significant bit set to digital high (e.g. 1) with all lower bits set to digital low (e.g. 0). If the analog signal is greater than the midway point, the most significant bit remains set at digital high and the next most significant bit is set to digital high for the next approximation. This next approximation is converted to an analog voltage signal by the internal DAC and compared to the analog signal sample. If the analog signal sample is still greater than the next approximation, the next most significant bit remains set at digital high. If the analog signal sample is less than the next approximation, the next most significant bit is set at digital low. After setting the next most significant bit based on the comparator output, the comparison process continues bit-by-bit until all bits have been set and a digital output is produced. The digital output is the converged upon digital value of the input voltage.

The next analog signal sample point will not be digitized until the conversion cycle for the current analog signal sample is complete. The bit-by-bit binary search process repeats for the next input signal sample during the next conversion cycle by resetting the initial approximation of the analog signal to the full-range midway point. Each conversion cycle uses all bits covering the full range of the A/D converter. Each conversion cycle, therefore, is started with an initial approximation equal to the midway point of the A/D converter full scale range and requires a bit time equal to N where N is the total number of bits spanning the full scale range.

In contrast, the self-adjusting A/D converter 202 disclosed herein uses an adaptable initial approximation of Mi and/or an adaptable bit number for converting Ai to the digital value Mi. ASAR 202 receives as input a bit control parameter, referred to herein as "BIT CONTROL" 224 and an initial digital approximation Minitial 222 of Ai from conversion control module 220. Methods performed by ASAR 202 and conversion control module 220 for adjusting BIT CONTROL 224, adjusting the adaptable bit number used for each conversion cycle, and setting the initial approximation Minitial 222 will be described below in conjunction with FIGS. 5 and 6.

ASAR logic 206 sets the number of bits used out by adaptable bit register 208 for each conversion cycle according to BIT CONTROL 224 received from conversion control module 220. BIT CONTROL 224 is an adjustable number set by conversion control module 220 and used by ASAR logic 206 to set the adapted bit number equal to or less than the total number of available bits corresponding to the full scale range of A/D converter 200. For example, if A/D converter 200 has an 8 bit resolution over a full range of ±Vref, the adapted bit number may be 8 bits or less. A fewer number of bits than the total number of available bits are used for at least some conversion cycles to shorten the overall average conversion cycle time and reduce power consumed by A/D converter 200.

ASAR logic 206 provides the initial approximation Minitial 222 to adaptable bit register 208. Minitial 222 is set equal to the most recent previous digital output Mout 230 in some examples. Alternatively, Minitial 222 may be set as a function of one or more most recent digital outputs. In this way Mi, the digitized value of Ai generated by ASAR 202, is initially approximated based on the digital value(s) of a predetermined number of most recent digitized output values Mout 230 of Vin 201. When Minitial 222 is set equal to Mout 230 from the most recent previous conversion cycle, it is assumed that Vin 201 does not vary rapidly relative to the sampling rate of track and hold circuit 214.

Without changing the bit resolution of NC converter 200, the number of bits used by adaptable bit register 208 for generating Mi 216 is set by ASAR logic 206. An adapted bit number that is less than the total number of available bits has a range that is a portion of the full scale range of A/D converter 200 that is less than the full scale range. The bit resolution is the same regardless of the number of bits used. The range of the adapted bit number may be centered on the initial approximation of Mi in some examples. In other words, the adapted bit number may have a range that is not centered on the mid-way point of the full scale range.

The initial digital approximation Minitial 222 is converted to an analog signal by DAC 210 to produce Vdac 205 as input to comparator 212. Vdac 205 is compared to Ai 215 by comparator 212. The output of comparator 212 is provided as feedback to ASAR logic 206, which responds by controlling adaptable bit register 208 to set the current bit to digital high if Ai 215 is greater than Vdac or digital low if Ai 215 is less than Vdac 205. ASAR logic 206 increments or decrements the next approximation of Ai based on the current bit value. For example, if the adaptable bit number has been adjusted to 4 bits, the next approximation of Ai 215 will be incremented or decremented from Minitial by 8 digital units, half of the 16 digital units of the most significant bit of the four bits.

The digital word representing the next approximation of Ai 215 is provided to DAC 210, converted to an analog signal Vdac 205, and compared to Ai 215 by comparator 212. The result of the comparison is used to adjust the next approximation up or down by half the current bit resolution. This process continues until all bits of the adjusted number of bits have been set.

Figure 4:
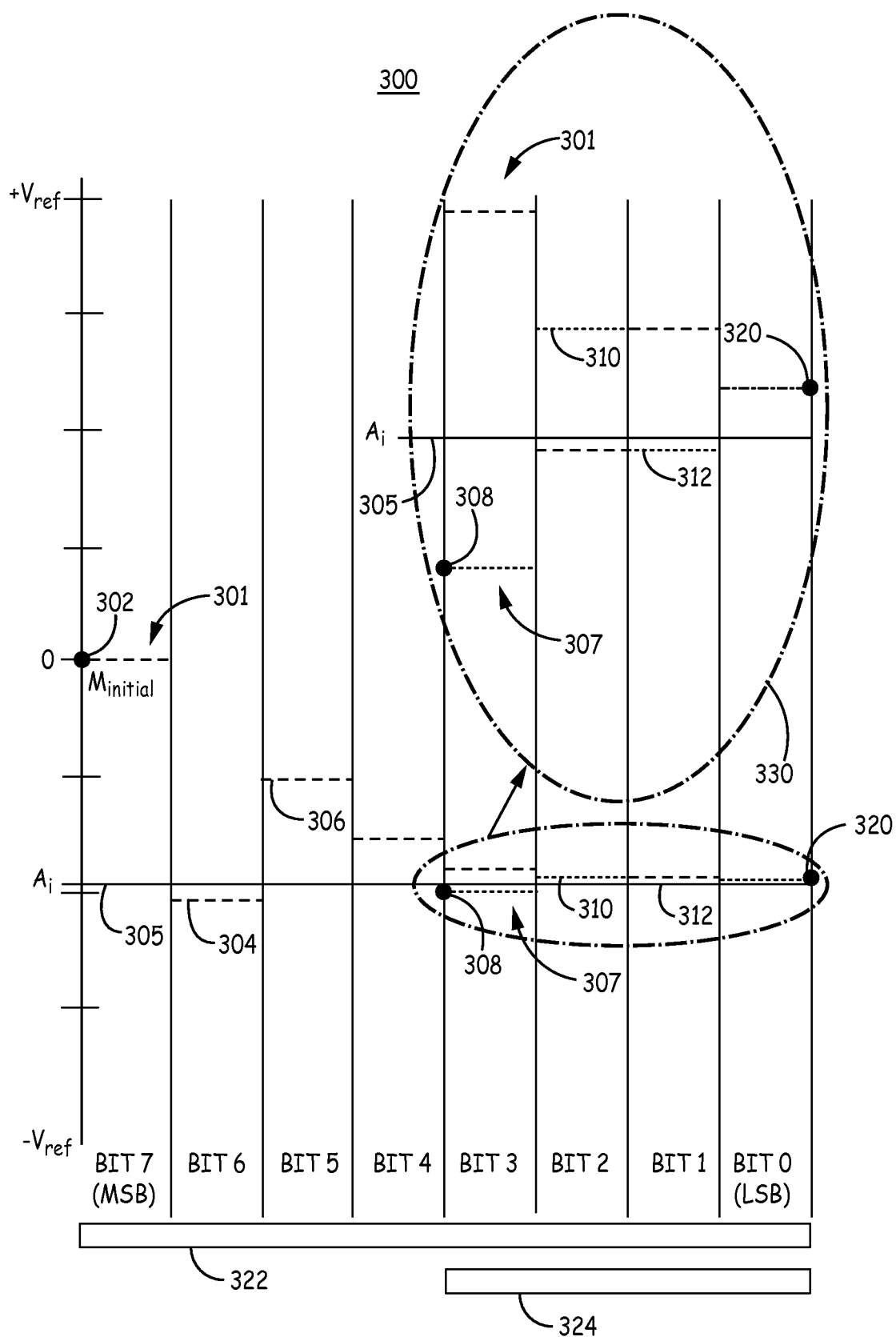
FIG. 4 is an illustrative plot of analog-to-digital conversion cycles during a full-range, full-bit conversion and during a partial range, adapted bit number conversion.

Examples of successive approximations of Ai 215 during a binary search for Mi 216, the digital value of Ai 215 generated by ASAR 202, are shown and described in conjunction with FIG. 4. After all of the bits of the adapted bit number are set, ASAR logic 208 determines the binary search is complete and provides the converged value Mi 216 to conversion control logic 220.

ASAR logic 206 may count the number of times the approximation of Ai is successively decremented or successively incremented during the binary search. This count is referred to here as the "successive adjustment count" and is an indication of whether Ai 215 is within the range of the adapted bit number being used for the conversion cycle. As will be further described below, this successive adjustment count, provided as the output COUNT 218 by SAR 202, is used by conversion control module 220 to determine BIT CONTROL 224, used for setting the adjusted number of bits during the next conversion cycle. For example, if COUNT indicates Ai 215 is outside the range of the adapted bit number, the bit number will be increased on the next conversion cycle.

COUNT 218 indicates whether Ai 215 is likely within the range of the adapted bit number used for the ith conversion cycle and represents one method for making this determination. To illustrate, if COUNT 218 is equal to the adjusted number of bits, this count indicates that every successive approximation of Ai 215 during the binary search was adjusted in the same direction, either always increased or always decreased. For example, the approximation of Ai was repeatedly and sequentially increased in response to every bit comparison of Vdac 205 to Ai 215 or it was sequentially and repeatedly decreased in response to every bit comparison. Ai was either always greater than every successive approximation or always less than every successive approximation during the bit-by-bit search for Mi. This indicates Ai 215 is likely outside the range of the adapted bit number, i.e. either greater than or less than the range of the adapted bit number.

If the COUNT 218 indicates Ai 215 is likely to be out of the range of the adapted bit number, the conversion control module 220 determines that the conversion cycle is not complete. Conversion control module 220 may set BIT CONTROL 224 to the maximum number of bits available, and a full bit conversion is performed over the full scale range of A/D converter 200 by ASAR 202. The full bit conversion may be performed starting with the same initial approximation Minitial as the previously attempted conversion cycle. Alternatively, the full bit conversion may be performed starting with an initial approximation Minitial 222 equal to a mid-way point of the full A/D converter range. The output Mi 216 of the full bit conversion is then provided by A/D converter 200 as the digital output value Mout 230 of Ai 215.

If COUNT 218 is less than the adapted bit number at the end of a given conversion cycle, Ai 215 is likely within the adapted bit range because the convergence involved at least one successive approximation of Ai 215 being adjusted in an opposite direction as a previous approximation of Ai 215. For example, an approximation of Ai 215 set by SAR logic 206 may have been increased in response to one bit comparison and decreased in response to a subsequent bit comparison. A sequence of successive approximations of Ai 215 that includes at least one change in direction indicates the binary search converged upon Ai within the adapted bit number range. The value of Mi 216 at the end of the conversion cycle is then deemed a valid digital representation of Ai 215. The ith conversion cycle is determined to be complete by conversion control module 220. The final approximation $M_i$ 216 converged upon by ASAR 202 during the binary search using the adapted bit number is provided as the digital output signal Mout 230 for the ith signal sample Ai 215 by conversion control module 220.

The embodiments described herein utilize an ASAR performing successive approximations during a binary search for Mi 216. In other embodiments, other non-binary search algorithms could be used. For example, the successive approximation could determine two bits at a time, in order to speed the processing. This would require multiple comparators to operate at each comparison point, and multiple quantized levels of voltage (or current, charge, etc.) to be generated for comparison purposes. Furthermore, it is contemplated that aspects of the techniques disclosed herein could be implemented using other types of A/D converters besides converters that use a successive approximation register.

FIG. 4 is an illustrative plot 300 of two different A/D conversion cycles. The A/D converter in this example has an 8 bit resolution over the A/D converter full scale range of −Vref to +Vref. One conversion cycle 301, shown by dashed line, is a full scale range, 8-bit conversion. The other conversion cycle 307, shown by dotted line, is a partial range, adapted bit number conversion The starting point 302 of conversion cycle 301 is the initial approximation Minitial of Ai 305. Minitial 302 is equal to the midway point (0 V in this example) of the full scale range, −Vref to +Vref. This initial approximation 302 is set by setting the most significant bit (MSB) 7 to digital high (e.g., 1) and setting all other bits to digital low (e.g., 0). Upon comparing the initial approximation 302 to Ai 305, the ASAR logic sets the MSB to digital low because Ai 305 is less than the initial approximation 302. ASAR logic decreases the next approximation 304 of Ai 305 by setting the next most significant bit to digital high. Since approximation 304 is less than Ai 305, the ASAR logic will increment the next approximation 306, and so on. This binary search process continues bit-by-bit for all eight bits.

A portion of conversion cycles 301 and 307 is shown with an enlarged vertical scale in the ellipse 330. The enlarged scale enables the convergence of the successive approximations following each bit comparison to be more easily viewed.

As shown in FIG. 4, the full bit conversion 301 converges on a final value Mi 320. The total time duration 322 of the conversion cycle 301 is the time required to compare and set all 8 bits to the digitized output value Mi 320. This duration 322 may be referred to as the bit time, which is 8 in this example.

An adapted bit number conversion cycle 307 starts at point 308. In this example, the bit number has been automatically adjusted to 4 based on previous conversion cycles as will be described in conjunction with FIGS. 5 and 6. The adapted bit number changes the range over which conversion is performed. The adapted bit number is not an adjustment of the bit resolution; each bit retains the same resolution such that the adapted bit number encompasses a reduced portion of the full scale range with an unchanged resolution per bit. In other words, if the full scale range is 20 mV, e.g. from −10 mV to +10 mV, and the total number of available bits is 8, the bit resolution is approximately 0.08 mV per bit (20 mV divided by 256). If the bit number is adjusted to four bits, the bit resolution will still be approximately 0.08 mV per bit, but the range over which the analog signal is converted will be reduced to a 10 mV range. This 10 mV range is not necessarily centered on 0 mV as is the full scale range. The adjusted number of bits sets the range of the adapted bit number to portion of the full scale range that is less than the range spanned by all 8 available bits. The adapted bit number range includes the initial approximation 308. The initial approximation 308 of the adapted conversion cycle 307 may be the center of the adapted bit number range in some examples.

The initial approximation Minitial represented by point 308 in the adaptive conversion cycle 307 is set to the previous digitized value of Ai−1 determined on the most recent, previous conversion cycle. In some cases, the analog input signal is not expected to change rapidly relative to the sampling rate. Accordingly, setting the initial approximation Minitial at the most recent previous digital output value Mout and using a reduced number of bits reduces the range over which the binary search is performed and starts the binary search at a reasonable predicted value of Mout. This narrowed binary search can reduce the conversion time required to converge on the digital value of Ai 305 since fewer bits are being used.

Each bit 0 through bit 3 is set by ASAR logic as needed to set Minitial 308, which is converted to an analog signal Vdac by the DAC for comparison to Ai 305. Upon the first comparison during the binary search, Minitial 308 is less than Ai 305. ASAR logic will increment the next approximation 310. The next approximation 310 is decremented by half the current bit value. For example, for bit 3, the next digital approximation of Ai 305 will be decreased by 4 digital units (half of 8). Since Ai 305 is less than the next approximation 310, the ASAR logic decreases the next successive approximation 312 by half the current bit value.

The final approximation is the converged upon digital value Mi 320 of Ai 305. The final values of Mi 320 for the full bit conversion cycle 301 and the adapted bit number conversion cycle 307 also converge, typically to the same digital value though there may be instances wherein the final converged value of the full bit conversion cycle 301 and the adapted bit conversion cycle 307 may be different.

The adapted bit number conversion cycle 307 has a bit time duration of four, significantly shorter than the full-range 8-bit conversion cycle duration 322. Thus, by using an adapted bit number, a digital value Mi 320 of Ai 305 can be generated consuming less time and power.

Figure 5:
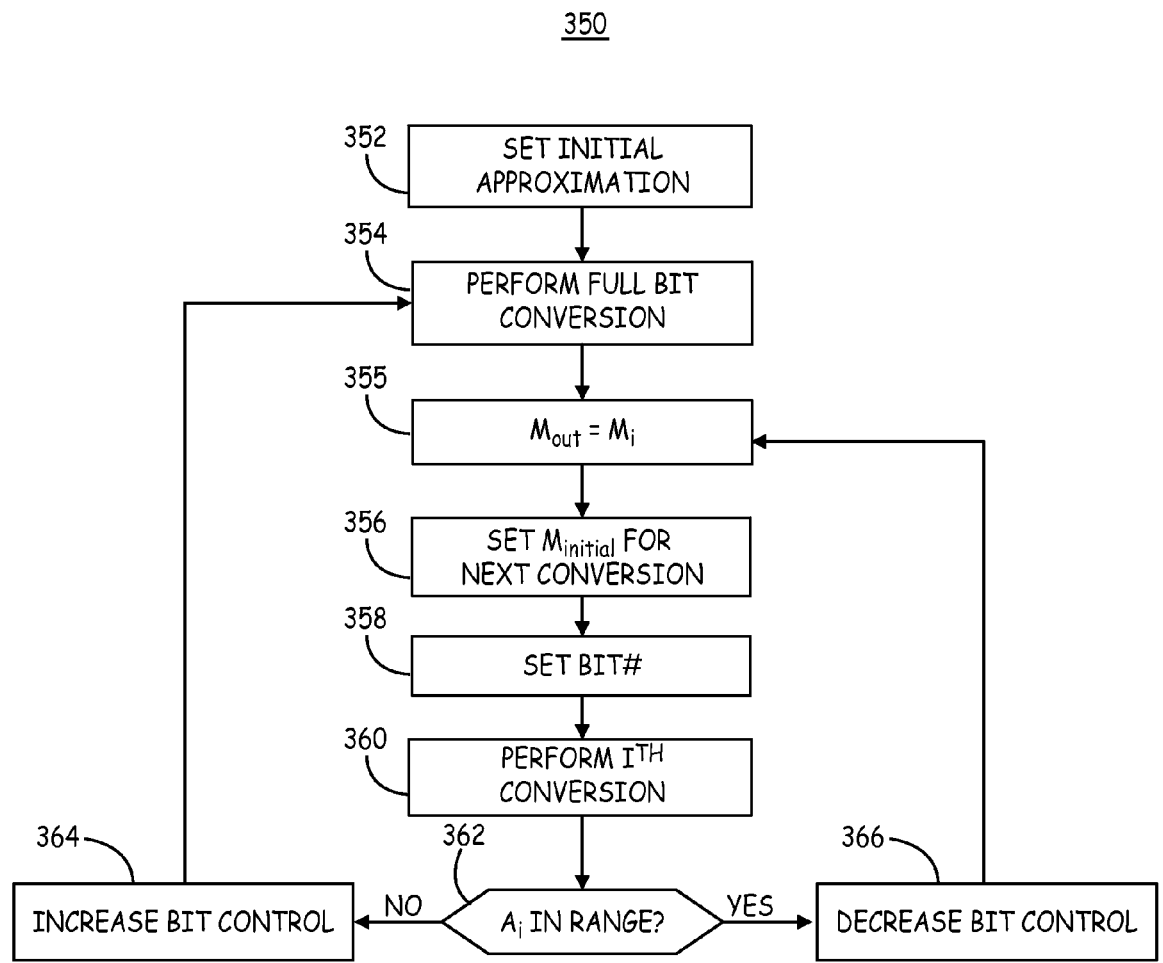
FIG. 5 is a flow chart of a method performed by a self-adjusting A/D converter according to one embodiment.

FIG. 5 is a flow chart 350 of a method for controlling a self-adjusting A/D converter according to one embodiment. At block 352, an initial approximation, Minitial, is set for the first conversion cycle upon enabling the A/D converter to digitize an analog input signal. Minitial for the first conversion cycle is a "guess" of Ai, the ith analog signal sample. On the first conversion cycle, when the A/D converter is initially enabled, a full bit conversion is performed as indicated at block 354 to determine Mi through a binary search. A full bit conversion is a conversion cycle that uses all available bits across the full range of the A/D converter in the bit-by-bit binary search. The initial approximation of Mi may be selected at block 352 as the mid-way point of the full range of the A/D converter. The binary search algorithm will converge on a value of Mi closest to the input signal sample Ai within the bit resolution of the A/D converter. After the full bit conversion cycle, the digital output signal Mout produced by the A/D converter is set equal to the converged value of Mi (block 355).

After performing this first conversion cycle, the initial approximation Minitial for the next conversion cycle is set at block 356. The initial approximation Minitial is set based on the digital output value Mout of at least one previous conversion cycle. Instead of starting each conversion cycle at the mid-point of the full scale range of the A/D converter, a starting prediction of Mi is made based on one or more recent Mout values. In one example, Minitial is set equal to Mout from the most recent previous conversion cycle (the ith−1 cycle). In other examples, Minitial may be set equal to a mean, median, mode, xth largest absolute value out of y recent values, or another value based on a combination of a predetermined number of previous Mout values.

At block 358, the self-adjusting A/D converter sets the adaptable bit number for the next conversion cycle. The adaptable bit number may be based on whether or not the previous converged value of Mi output by SAR logic was within a range of the bit number used on the previous conversion cycle, as will be described below and in conjunction with FIG. 6. After the first conversion cycle, the bit number may remain at the full scale bit number for the second conversion cycle. In other embodiments, the bit number may be reduced on the next conversion cycle, for example by one bit.

At block 360, the next (ith) conversion is performed by performing a binary search beginning at Minitial set for the current conversion cycle and using the number of bits set at block 358. After converging on Mi, the SAR logic determines whether the value of Ai is likely within range of the number of bits used for the current conversion cycle. If the bit number has been reduced from the total number of available bits at block 358, the adapted bit number has a range that is a portion less than the full scale range of the A/D converter, with each of the bits in the adjusted number of bits having the same bit resolution as the bit resolution assigned to each bit in the full scale range. In some instances, an input signal sample Ai may fall outside the adapted bit number range but within the full scale range of the A/D converter. If this happens, the bit number needs to be increased to obtain a correct value of Mi for Ai. However, as long as Ai remains in the range of the adapted bit number, A/D conversion can continue using a reduced number of bits thereby reducing the overall average conversion cycle time and A/D converter power consumption.

In one embodiment, determining whether Ai is within the current bit number range is made by the conversion control module by determining if all adjustments to the approximation of Mi were made in the same direction. For example, if all successive approximations of Mi during a binary search were increased from the previous approximation, Ai is likely greater than an upper boundary of the adapted bit number range. Likewise, if all successive approximations of Mi were decreased from the previous approximation, Ai is likely less than a lower boundary of the adapted bit number range.

Other methods for determining whether Ai is likely out of the current bit number range may be used. For example Mi may be compared to the boundaries of the current bit number range. If Mi is equal to a boundary value, Ai is deemed likely to be out of range.

If Ai is determined to likely be out of an adapted bit number range at block 362, a control parameter used by the conversion control module for controlling the adaptable bit number on each conversion cycle is increased at block 364. If Ai is out of the bit number range, the adaptable bit number is increased on the next conversion cycle in an attempt to capture Ai within the adapted bit number range.

In some embodiments, prior to advancing to the next conversion cycle to digitize $A_{i+1}$ using the increased, adapted bit number, the ith conversion cycle will be repeated by returning to block 354. Since Ai was determined to be out of the adapted bit number range, the value of Mi at the end of the ith conversion cycle may not be the correct digital value of Ai. The ith conversion cycle may be repeated using a broader range, i.e. a larger bit number, to obtain a correct value of Mi for the current signal sample Ai. A full bit conversion may be performed at block 354 to obtain a valid value Mi, within the full scale A/D converter range. Alternatively, the adaptable bit number may be increased by one or another predetermined increment for repeating the ith conversion cycle with a larger bit number spanning a larger portion of the full scale range of the A/D converter. After repeating the ith conversion cycle using an increased number of bits at block 354, the digital output signal Mout is generated at block 355, equal to the valid Mi value resulting from the repeated conversion cycle.

In some instances, the bit control parameter may already be at a maximum value, for example when the last conversion cycle was a full bit conversion. If Ai is outside the full scale range of the A/D converter, e.g. due to noise, all available bits will be used until Ai is within range again.

If Ai is within the current bit number range, as determined at block 362, the bit control parameter is decreased at block 366. A decreased bit control parameter will be used to decrease the adaptable bit number on the next or another subsequent conversion cycle as long as Ai remains within an adapted bit number range. Techniques for controlling how often the adaptable bit number is decreased in response to Ai being within a current bit number range are described in greater detail in conjunction with FIG. 6.

After decreasing the bit control parameter, the A/D converter process returns to block 355 to generate Mout equal to the Mi result of the adapted bit number conversion cycle. As long as Ai is determined to be within the adapted bit number range, the value of Mi converged upon at the end of the shortened binary search is deemed a valid digital value of Ai. Minitial is set for the next conversion cycle, e.g. using Mi, at block 356.

The adaptable bit number is set at block 358. The adapted bit number may remain the same for a desired number of cycles before decreasing the bit number in response to Ai being within the adapted bit number range. For example, the bit number may be decreased every Zth cycle if Ai has been within adapted bit number range for Z conversion cycles. Alternatively, the bit number may be reduced each time Ai is within an adapted bit number range. A faster reduction of the adaptable bit number may result in more frequent full bit conversions due to Ai being out of range of an adapted bit number. However, too slow of a reduction in the adaptable bit number may limit the benefit of reduced conversion time. Accordingly, the rate that the adaptable bit number is reduced may be optimized to strive for a maximum reduction in overall conversion time and this rate may be automatically adjusted by the A/D converter as well.

Figure 6:
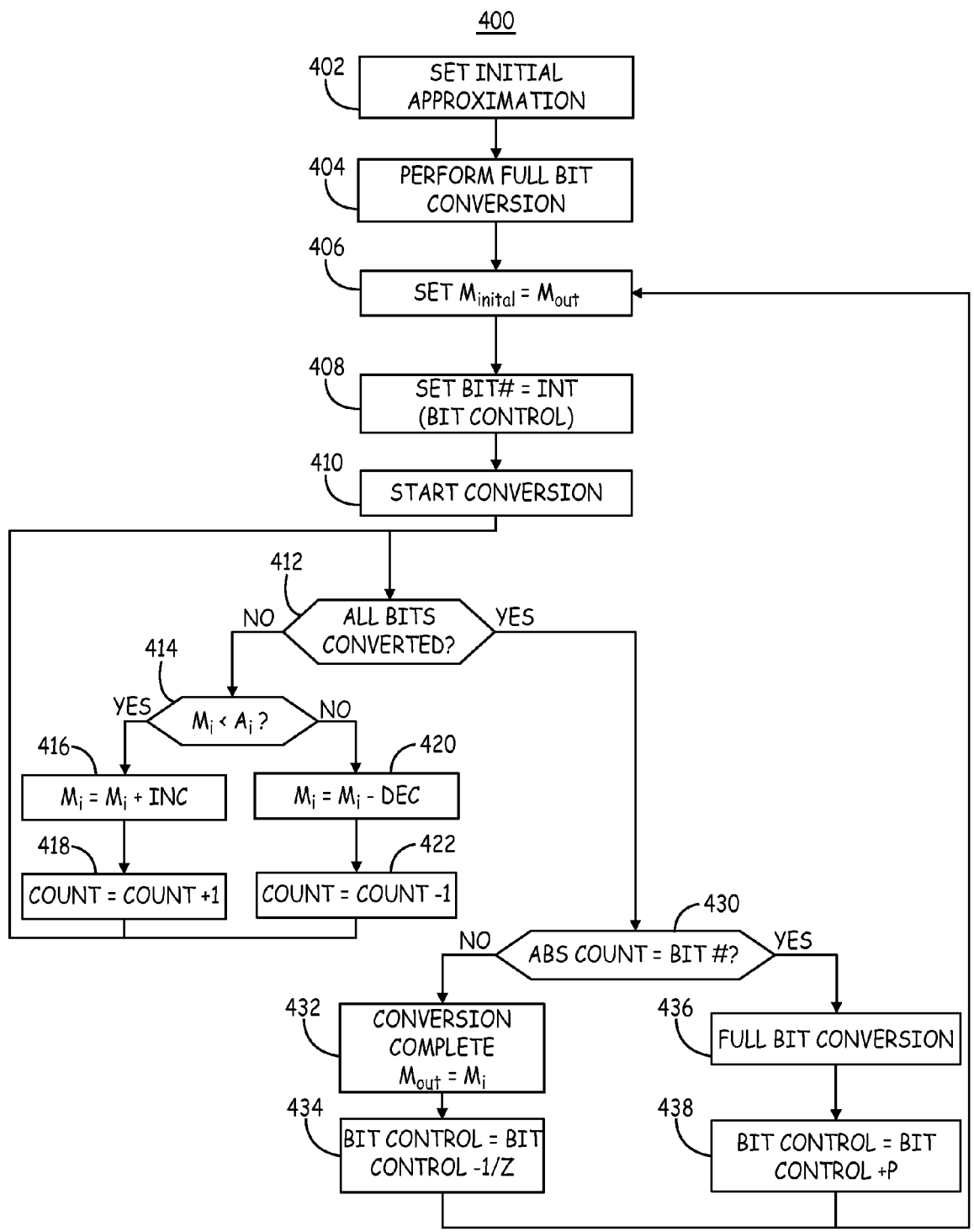
FIG. 6 is a flow chart of a method for controlling A/D conversion using an adaptable bit number according to one embodiment.

FIG. 6 is a flow chart 400 of an example A/D conversion method performed by a self-adjusting A/D converter that includes an adaptable bit number. As described above, when IMD 10 is initially enabled to begin A/D conversion of an analog signal, the first sample point of an analog signal may be converted using all available bits spanning the full-scale A/D converter range. Since no previous digitized value of the input signal is known, an initial approximation may be set at block 402 as the midway point of the full range, e.g. 0 V in a full scale range from −Vref to +Vref or Vref/2 in a full scale range from 0 to Vref.

After performing a full bit conversion for the first sample point at block 404, the first approximation Minitial for the next conversion cycle may be set to the first digitized value Mout at block 406, i.e. to the result of the previous conversion cycle performed at block 404. The number of bits used for the next conversion is set by the ASAR logic according to a bit control parameter provided by the conversion control module at block 408. Computation of the bit control parameter (BIT CONTROL) by the conversion control module is described in greater detail below. ASAR logic sets the number of bits (BIT#) used by the ASAR bit register during the next conversion cycle based on the bit control parameter. In one example, BIT# is set by rounding BIT CONTROL down to the nearest integer (INT(BIT CONTROL)) as shown in the example at block 408.

After setting the initial approximation Minitial equal to the previous Mout at block 406 and setting the adapted bit number at block 408, the next conversion cycle begins at block 410. A bit-by-bit binary search may be performed until all bits of the adapted bit number are converted. If all bits of the adapted bit number have not yet been converted, as determined at decision block 412, successive approximations of $A_i$, beginning with Minitial, are compared to the current analog signal sample $A_i$ at block 414. If the approximation Mi is greater than $A_i$ for the current bit comparison (decision block 414), the successive approximation $M_i$ is increased from its current value by an increment (INC) associated with the current bit value, e.g. half the current bit value, at block 416.

At block 418, a counter included in the ASAR logic is increased by one. This counter may be referred to as a "successive approximation counter" because it is used to count the number of times the approximation $M_i$ of Ai is repeatedly and sequentially adjusted in the same direction, i.e., successively increased or successively decreased. As described below, this count is used by the conversion control module to control when the adaptable bit number is increased to the maximum number of available bits. The current bit value will be set to digital high when Ai is greater than the current approximation Mi.

If the current approximation $M_i$ is less than $A_i$ (decision block 414), the approximation $M_i$ used for the next comparison is decreased at block 420 from its current value by a decrement (DEC) associated with the current bit value, e.g. half the current bit value. The current bit value will be set to digital low. The successive adjustment count is decreased by one at block 422 when the approximation Mi is decreased.

If the approximation $M_i$ is repeatedly increased on successive bit conversions, the count will reach the BIT# at block 418. In other words, if Ai is greater than Mi for every comparison during the bit-by-bit binary search, the successive approximations of Mi will all be increased, resulting in the count reaching the bit number. Similarly, if the approximation $M_i$ is successively decreased on every bit conversion during the bit-by-bit binary search, the count will reach the negative value of the bit number at block 422. If the approximation of $M_i$ is increased on at least one bit conversion and decreased on at least one bit conversion during the current conversion cycle, the count will reach a value less than the bit number.

After all bits are converted, as determined at block 412, the absolute value of the successive approximation counter is compared to the bit number at block 430. If the absolute value of the count has reached the bit number, indicating the conversion required sequentially increasing successive approximations Mi for every bit or sequentially decreasing successive approximations Mi for every bit, a full bit conversion is performed at block 436. Successively increasing approximations or successively decreasing approximations for all bit comparisons indicates Ai is outside the adapted bit number range. A full bit conversion is performed because the signal sample $A_i$ is out of the range of the current bit number, in either the positive or negative direction. The full bit conversion at block 436 allows a digitized representation of $A_i$ to be obtained within the full scale range of the A/D converter. The output Mout of the full bit conversion becomes the initial approximation Minitial for the next conversion cycle upon returning to block 406.

In response to performing the full bit conversion due to the adapted bit number range not encompassing the ith signal sample $A_i$, the conversion control module increases the bit control parameter at block 438. The amount P that the bit control parameter is increased in response to a full bit conversion may vary between embodiments and may be a programmable or adjustable number. In one example, BIT CONTROL is increased by one. In this way, each time an out of range condition is reached as indicated by the successive approximation counter reaching the bit number, BIT CONTROL is increased by one thereby increasing the bit number by one for the next conversion cycle. This allows the adjustable bit number to be rapidly increased on succeeding conversion cycles until the bit number range includes the incoming analog signal or the maximum available number of bits is reached.

In some embodiments, the amount P that the bit control parameter is increased at block 438 is a fixed value. Alternatively, the amount P that BIT CONTROL is increased at block 438 may be scaled or adapted in response to the output of the full bit conversion performed at block 436. For example, the output Mout of the full bit conversion may be compared to previous Mout values. If there is a relatively large difference between Mout for the full bit conversion and the previous Mout value, the bit control parameter may be increased by more than one to cause the ASAR logic to increase the bit number more quickly for a more rapidly varying signal. The difference between Mout for the current conversion cycle and a previous conversion cycle may be compared to a threshold, range, or the bit resolution for determining the increment P applied to the bit control parameter. Generally, if sequential Mout values indicate a relatively high slope of Vin, the bit control parameter may be increased by a greater increment that when sequential Mout values indicate a relatively lower slope of Vin.

After adjusting the bit control parameter at block 438, the A/D conversion process returns to block 406 to set Minitial for starting the next conversion cycle. Minitial may be set to the output Mout of the full bit conversion performed at block 436. The bit number for the next conversion cycle is set to the integer value of the bit control parameter at block 408. The next conversion cycle starts at block 410 and proceeds as described previously.

If the absolute value of the successive approximation counter is not equal to the bit number at the end of a conversion cycle, as determined at block 430, the conversion is deemed complete by the conversion control module. The digitized value of the final approximation $M_i$ generated by the ASAR is received by the conversion control module and produced as the Mout signal provided to the IMD processor and control module (or other control or processing circuitry) from the A/D converter. A count less than the bit number indicates the adapted bit number search converged on a value of Ai within the range of the adapted bit number.

At block 434, BIT CONTROL is decreased. The amount by which BIT CONTROL is decreased may vary between embodiments and may be a fixed or adjustable number. In the example shown, the bit control parameter is reduced from its current value by 1/Z where Z may be a fixed or programmable number. Z may alternatively be an automatically adjustable number. For example, IMD 10 may be configured to "learn" an optimal value for Z for minimizing conversion time for a given analog input signal for a given patient. Z may be any value greater than zero and will typically be, without limitation, an integer value greater than or equal to one.

After adjusting the bit control parameter, the A/D conversion process returns to block 406 to set Minitial for the next conversion cycle to the most recent digitized value of Ai (provided as Mout) at block 432. The bit number for the next conversion cycle is set to the integer value of the bit control parameter. Accordingly, if a fractional portion 1/Z has been subtracted from the previous BIT CONTROL value, the BIT CONTROL value is rounded down to the nearest integer to set the adjusted bit number. The next conversion cycle begins at block 410 using the initial approximation Minitial and BIT# set at block 406 and 408 respectively.

The value of Z is used by the conversion control module to control how frequently the bit number is decreased. For example, when Z is greater than or equal to one, assuming no intervening full bit conversions are required that would cause an increase in the BIT CONTROL at block 438, the BIT CONTROL is reduced by 1/Z on each successive conversion cycle. If BIT CONTROL is reduced by 1/Z for Z sequential conversion cycles, BIT# will be reduced by one on the Zth conversion cycle. As such, if Z is equal to or greater than 1, the maximum frequency that the bit number is decreased at block 408 is every Zth conversion cycle.

In instances that Z is greater than 1 and P is equal to 1, the BIT CONTROL parameter causes the adapted bit number to increase relatively more rapidly in response to an out-of-range result of a conversion cycle and decrease relatively less rapidly when the conversion remains within range of the adapted bit number. Reducing the bit time required for a conversion cycle by using an adapted bit number reduces the total power consumption required for A/D conversion. Even though a conversion cycle may need to be repeated using all available bits in response to the successive approximation counter reaching the bit number, the overall conversion time may still be reduced since a full range conversion is not performed for every single conversion cycle.

Figure 7:
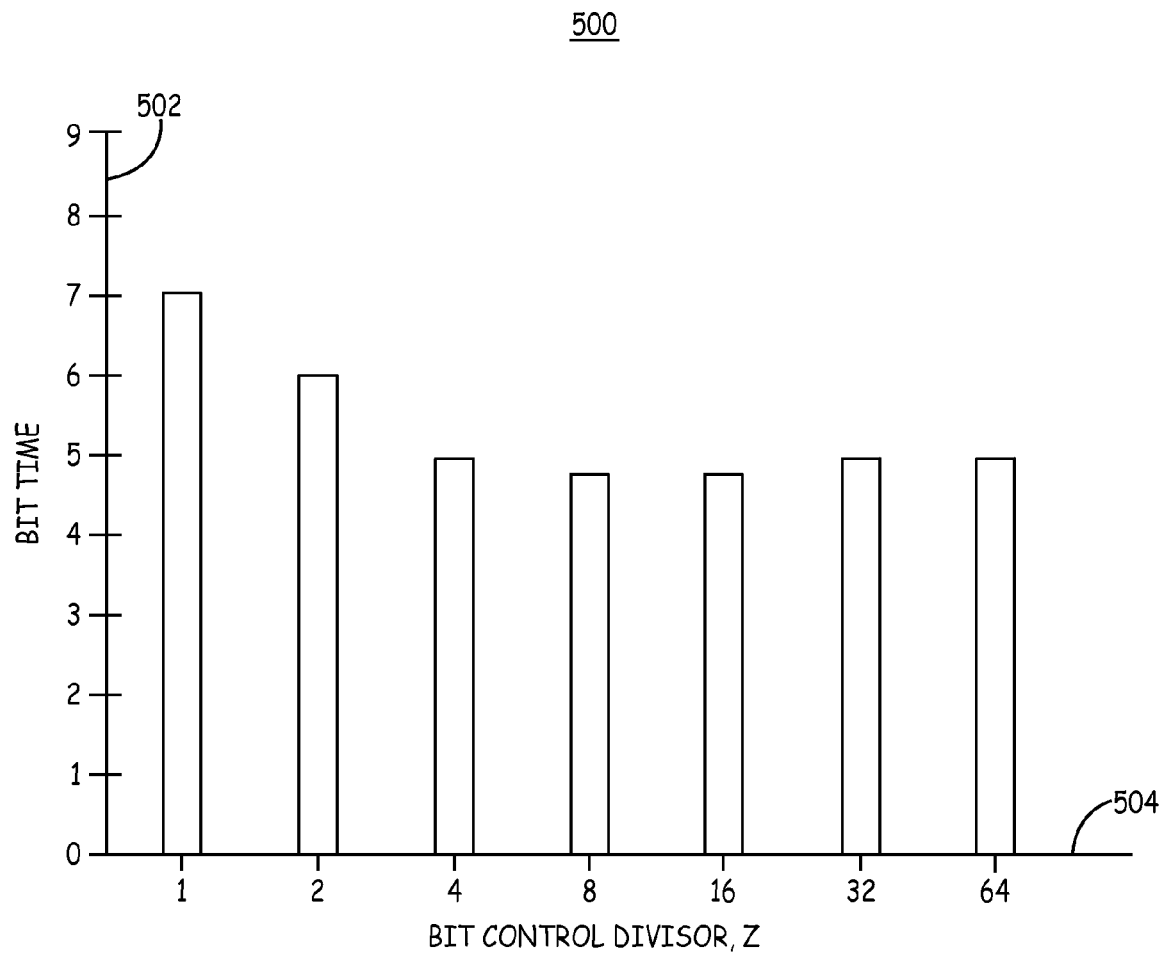
FIG. 7 is a plot of bit time usage for varying values of a divisor Z used to adjust a bit number control parameter.

FIG. 7 is a plot of bit time usage for varying values of the divisor Z used to adjust the BIT CONTROL parameter at block 434 of FIG. 6 according to one illustrative example. The average bit time used for all conversion cycles is plotted along the y-axis 502 for the A/D conversion of an analog accelerometer signal implanted in standing and running subjects. The average bit time indicates the overall average number of bits being used per conversion cycle when the adaptable bit number is being adjusted according to a bit control parameter as described in conjunction with FIG. 6. The example shown includes a total number of nine available bits, used for an initial full-range conversion and for any full bit conversions performed if the analog signal is out of range of an adapted bit number range.

The bit control divisor Z is plotted along the x-axis 504. The divisor Z is used to decrement the bit control parameter in the equation BIT CONTROL=BIT CONTROL−1/Z, as described in conjunction with block 434 of FIG. 6. As can be seen in FIG. 7, all values tested for Z, even the value of 1, resulted in an overall decrease in the average bit time for all conversion cycles as compared to doing a full bit conversion on all conversion cycles. For example, when Z=1, the average bit time was reduced to 7. When Z was 8 or 16, the average bit time was reduced to less than 5.

Z may be a fixed or adjustable value in various examples. The value selected for Z may be different for different signals being converted by an A/D converter included in IMD 10. Depending on the analog signal behavior and other factors, the optimal Z for achieving the greatest reduction in bit time compared to a full bit conversion on every cycle may vary between signal type, sampling rates, between patients, and over time due to other factors influencing the analog signal. Accordingly, Z may be an adjustable value. In some embodiments, the IMD 10 may store bit time data for varying values of Z to "learn" the optimal value of Z for reducing average bit time for converting a given signal. The optimal Z may be automatically set by the IMD 10.

Figure 8:
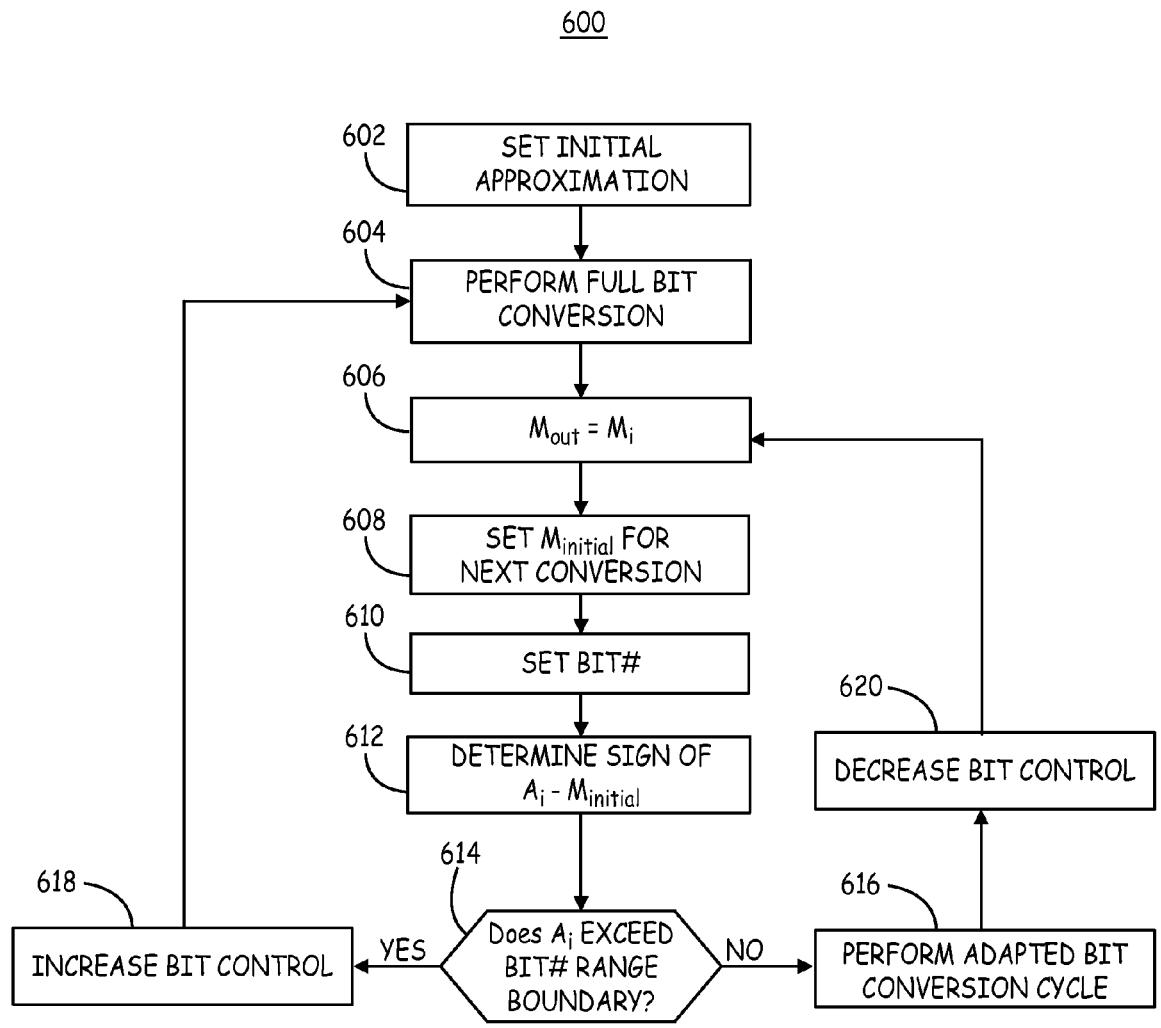
FIG. 8 is a flow chart of a method for controlling a self-adjusting A/D converter according to another embodiment.

FIG. 8 is a flow chart 600 of a method for controlling a self-adjusting A/D converter according to another embodiment. At block 352, an initial digital approximation of Ai, Minitial, is set for the first conversion cycle upon enabling the A/D converter to digitize an analog input signal. The initial digital approximation of Ai may be selected at block 602 as the mid-way point of the full range of the A/D converter. A full bit conversion is performed at block 604 using the full scale A/D converter range and all available bits. The digital output signal Mout produced by the A/D converter upon completing the full bit conversion is set equal to the converged value of Mi (block 606).

After performing the first conversion cycle, the initial approximation Minitial for the next conversion cycle is set at block 608. Minitial for the next conversion cycle may be set based on the digital output value Mout of at least one previous conversion cycle as described above. At block 610, the bit number is set for the next conversion cycle, which may be an adapted bit number based on Ai being within an adapted bit number range for a predetermined number of previous conversion cycles as described above.

At 612, the initial approximation Minitial is compared to Ai for the current conversion cycle. In some examples, this comparison is made by determining a difference between Ai and Minitial and determining the sign, either positive or negative, of this difference. The sign of the difference Ai−Minitial indicates if Ai is greater than Minitial (a positive difference) or if Ai is less than Minitial (a negative difference). The sign of this difference is used during the adapted bit number conversion cycle because it indicates the direction to adjust the next digital approximation of Ai. If the sign is positive, the next approximation will be increased, and if the sign is negative the next approximation will be decreased.

At block 614, Ai is compared to the boundary value of the adapted bit number range in the direction of the sign determined at block 612. For example, if the adapted bit number range is ±5 mV, and Ai is determined to be greater than Minitial (a positive sign difference), Ai is compared to the positive or upper boundary of the adapted bit number range, +5 mV in this example. If Ai is less than Minitial, resulting in a negative difference at block 612, Ai is compared to the negative or lower boundary of the adapted bit number range.

If Ai exceeds a boundary value of the adapted bit number range, i.e. is either greater than an upper boundary or less than a lower boundary as determined by the comparison at block 614, the bit control parameter is increased at block 618. A full bit conversion is performed at block 604 immediately, prior to completing the adapted bit number conversion cycle. If Ai does not exceed a boundary value, i.e. is not greater than an upper boundary or less than a lower boundary, the A/D converter proceeds with completing the adapted bit number conversion at block 616. The bit control parameter is decreased at block 620 for use in setting the bit number in the next conversion cycle.

By comparing Ai to a boundary value after an initial comparison to Minitial, an earlier determination of an out-of-range condition is detected than when the successive adjustment counter is used as described in conjunction with in FIG. 6. This earlier detection of an out-of-range condition enables a restart of the conversion cycle using the total number of available bits to occur earlier, rather than after completing the adapted bit number conversion cycle as described in conjunction with FIG. 6. The method shown by flow chart 600, however, does require an extra Ai comparison, the comparison of Ai to the boundary value of the adapted bit number range (block 614), for every adapted bit number conversion cycle.

Thus, various embodiments of an apparatus and method for A/D conversion have been described. However, one of ordinary skill in the art will appreciate that various modifications may be made to the described embodiments without departing from the scope of the claims. For example, although specific examples of conversion control parameters and parameter values have been described, it is recognized that other control parameters or parameter values may be defined or conceived for controlling an adaptable bit number and an initial approximation of a digital value of an analog signal sample for reducing the average time required for A/D conversion cycles. These and other examples are within the scope of the following claims.

The invention claimed is:

1. A method, comprising:
   receiving an analog signal by an analog-to-digital (A/D) converter having a full scale range and a total number of bits spanning the full scale range;
   converting the analog signal to a digital signal by the A/D converter over a plurality of conversion cycles using an adaptable bit number on at least a current conversion cycle of the plurality of conversion cycles, wherein the adaptable bit number comprises an adapted number of bits spanning a portion of the full scale range that is less than the full scale range of the total number of bits;
   determining whether a sample point of the analog signal is within the portion of the full scale range spanned by the adapted number of bits;
   decreasing the adaptable bit number used for a subsequent conversion cycle of the plurality of conversion cycles in response to the sample point of the analog signal being within the portion of the full scale range; and
   decreasing the adaptable bit number after a predetermined number of analog signal sample points are within the portion of the full scale range.

2. The method of claim 1, further comprising,
   setting an initial approximation of a digital value of a sample point of the analog signal using a previously digitized value of the analog signal; and
   searching for the digital value of the sample point starting from the initial approximation.

3. The method of claim 2, wherein the initial approximation is set equal to a digitized value obtained in an immediately preceding conversion cycle.

4. The method of claim 2, wherein the initial approximation is within the portion of the full scale range spanned by the adjusted number of bits.

5. The method of claim 1, further comprising:
  determining whether a sample point of the analog signal is outside the portion of the full scale range spanned by the adapted number of bits; and
  increasing the adaptable bit number for a subsequent conversion cycle of the plurality of conversion cycles if the analog signal sample point is outside the portion of the full scale range.

6. The method of claim 1, further comprising:
  determining whether a sample point of the analog signal is outside the portion of the full scale range spanned by the adapted number of bits; and
  repeating converting the analog signal to a digital signal using the total number of bits in response to the analog signal sample point being outside the portion of the full scale range.

7. The method of claim 1, further comprising adjusting the a predetermined number of analog signal sample points required to be in the portion of the full scale range before decreasing the adaptable bit number in order to decrease an overall time required to convert the analog signal over the plurality of conversion cycles.

8. The method of claim 1, further comprising:
  comparing an approximation of a digital value of a sample point of the analog signal of to the analog signal during a binary search;
  adjusting the approximation in a first direction in response to the approximation being greater than the analog signal and in a second direction in response to the approximation being less than the analog signal;
  producing a count of a number of successive approximations repeatedly adjusted in only one of the first direction and the second direction during the searching; and
  adjusting the adaptable bit number on a subsequent conversion cycle of the plurality of conversion cycles in response to the count.

9. The method of claim 1, further comprising receiving the analog signal from an implantable physiological sensor.

10. A medical device, comprising
  an analog-to-digital (A/D) converter configured to receive an analog signal and having a full scale range and a total number of bits spanning the full scale range,
  the A/D converter configured to convert the analog signal to a digital signal over a plurality of conversion cycles using an adaptable bit number on at least a current conversion cycle of the plurality of conversion cycles, wherein the adaptable bit number comprises an adapted number of bits spanning a portion of the full scale range that is less than the full scale range of the total number of bits, wherein the A/D converter is configured to:
  determine whether a sample point of the analog signal is within the portion of the full scale range spanned by the adapted number of bits;
  decrease the adaptable bit number for a subsequent conversion cycle of the plurality of conversion cycles if the sample point of the analog signal is within the portion of the full scale range, and
  decrease the adaptable bit number after a predetermined number of analog signal sample points are within the portion of the full scale range.

11. The device of claim 10, further comprising:
  a conversion control module configured to set an initial approximation of a digital value of a sample point of the analog signal using a previously digitized value of the analog signal,
  the A/D converter configured to search for the digital value of the sample point starting from the initial approximation.

12. The device of claim 11, wherein the conversion control module is configured to set the initial approximation equal to a digitized value obtained in an immediately preceding conversion cycle.

13. The device of claim 11, wherein the A/D converter is configured to set the adaptable bit number spanning the portion of the full scale comprising the initial approximation.

14. The device of claim 10, wherein the A/D converter is configured to:
  determine whether a sample point of the analog signal is outside the portion of the full scale range spanned by the adapted number of bits; and
  increase the adaptable bit number for a subsequent conversion cycle of the plurality of conversion cycles if the analog signal sample point is outside the portion of the full scale range.

15. The device of claim 10, wherein the A/D converter is configured to:
  determine whether a sample point of the analog signal is outside the portion of the full scale range spanned by the adapted number of bits; and
  repeat converting the analog signal to a digital signal using the total number of bits in response to the analog signal being outside the portion of the full scale range.

16. The device of claim 10, wherein the A/D converter is configured to adjust the predetermined number of analog signal sample points required to be within the portion of the full scale range before decreasing the adaptable bit number in order to decrease an overall time required to convert the analog signal over the plurality of conversion cycles.

17. The device of claim 10, wherein the A/D converter is configured to:
  compare a digital approximation a sample point of the analog signal to the analog signal;
  adjust the digital approximation in response to the comparison in a first direction in response to the digital approximation being greater than the analog signal and in a second direction in response to the digital approximation being less than the analog signal;
  produce a count of a number of successive digital approximations repeatedly adjusted in only one of the first direction and the second direction during the searching; and
  adjust the adaptable bit number on a subsequent conversion cycle of the plurality of conversion cycles in response to the count.

18. The device of claim 10, further comprising an implantable physiological sensor producing the analog signal.

19. A medical device, comprising:
  receiving means for receiving an analog signal;
  converting means for converting the analog signal to a digital signal over a plurality of conversion cycles; and
  controlling means for adjusting an adaptable number of bits used by the converting means for converting the analog signal over the plurality of conversion cycles, the adaptable number of bits spanning less than a full scale range of the converting means for at least one of the plurality of conversion cycles; and
  means for determining whether a sample point of the analog signal is within the portion of the full scale range spanned by the adapted number of bits;
  wherein the converting means is configured to decrease the adaptable bit number used for a subsequent conversion cycle of the plurality of conversion cycles in response to the sample point of the analog signal being within the portion of the full scale range; and decrease the adaptable bit number after a predetermined number of analog signal sample points are within the portion of the full scale range.

20. A non-transitory computer readable storage medium storing a set of instructions executable by a control module of an analog-to-digital (A/D) converter included in a medical device for causing the control module to:

enable the A/D converter to convert an analog signal to a digital signal over a plurality of conversion cycles using an adaptable bit number; and adjust the adaptable bit number for at least one of the plurality of conversion cycles to a number of bits that span a portion of a full scale range of the A/D converter that is less than the full scale range of the A/D converter spanned by a total number of available bits of the A/D converter;

determine whether a sample point of the analog signal is within the portion of the full scale range spanned by the adapted number of bits;

decrease the adaptable bit number used for a subsequent conversion cycle of the plurality of conversion cycles in response to the sample point of the analog signal being within the portion of the full scale range; and decrease the adaptable bit number after a predetermined number of analog signal sample points are within the portion of the full scale range.

* * * * *